(12) United States Patent
Mason et al.

(10) Patent No.: US 7,029,570 B2
(45) Date of Patent: Apr. 18, 2006

(54) DISAGGREGATION OF ASPHALTENES IN INCOMPATIBLE PETROLEUM OIL MIXTURES

(75) Inventors: Thomas G. Mason, Summit, NJ (US); Min Yue Lin, North Potomac, MD (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 0 days.

(21) Appl. No.: 10/699,232

(22) Filed: Oct. 31, 2003

(65) Prior Publication Data

US 2004/0089589 A1 May 13, 2004

Related U.S. Application Data

(63) Continuation of application No. 09/818,435, filed on Mar. 27, 2001, now abandoned.

(51) Int. Cl.
*C10G 31/00* (2006.01)

(52) U.S. Cl. .................. 208/48 R; 208/177; 250/301

(58) Field of Classification Search ............. 208/48 R, 208/117; 250/301
See application file for complete search history.

(56) References Cited

U.S. PATENT DOCUMENTS

| | | | | |
|---|---|---|---|---|
| 3,136,711 A | * | 6/1964 | Glaser et al. | 208/37 |
| 4,514,283 A | * | 4/1985 | Closmann et al. | 208/86 |
| 5,207,891 A | * | 5/1993 | Sung et al. | 208/44 |

OTHER PUBLICATIONS

Moschopedis, Speros E. et al., "Thermal Decomposition of Asphaltenes", 1978, Fuel, vol. 57, Issue 7, 431-434.*

* cited by examiner

*Primary Examiner*—Walter D. Griffin
(74) *Attorney, Agent, or Firm*—Ronald D. Hantman

(57) ABSTRACT

The thermal decomposition of Athabasca asphaltene at relatively low (<350° C.) temperatures is believed to proceed by elimination of groups situated on peripheral sites of the asphaltene. More severe degradation of the asphaltene structure does not occur until elevated (>350° C.) temperatures are attained.

14 Claims, 12 Drawing Sheets

DISAGGREGATION OF ASPHALTENES IN INCOMPATIBLE PETROLEUM OIL MIXTURES

This application is a continuation of U.S. Ser. No. 09/818,435 filed Mar. 27, 2001, now abandoned.

BACKGROUND OF THE INVENTION

The present invention relates to the disaggregation of asphaltenes. In particular, the present invention includes a method to determine aggregation and steps to disaggregate the asphaltenes.

Asphaltenes are a fraction of a petroleum oil or refinery process stream that typically aggregate or precipitate out of solution when a nonpolar solvent, petroleum oil, or process stream is mixed or blended with it. Asphaltenes represent a wide variety of hydrocarbon molecules that are typically polyaromatic in nature with some degree of alkylation present and which may or may not contain heteroatoms such as oxygen, nitrogen, and sulfur and metal atoms in their structures. Asphaltenes are usually found in significant quantities in heavy crude oils and refinery residua, and they are believed to sometimes self-assemble into colloidal micelle-like structures of several molecules that remain thermally suspended in solution due to their small size and possible solvating effects of other types of molecules in the petroleum oil or process stream. These micelle-like structures of several molecules are sometimes referred to as "asphaltene particles" in order to differentiate them from the single "asphaltene molecules" that may also be present in suspension in the oil. The asphaltene particles are typically smaller than twenty nanometers in size, but this can vary depending upon the source of the petroleum oil or process stream and their concentration in the oil.

It is well known that insoluble asphaltenes may precipitate when two or more unprocessed petroleum crude oils and/or refinery process streams are blended together. The term "asphaltene aggregate" refers to the formation of larger precipitated clusters of asphaltene particles and molecules that stick together due to an attractive interaction that has been introduced when the nonpolar petroleum oil and/or refinery process stream is blended into the oil containing the suspended asphaltenes. These asphaltene aggregates are typically a micron in size and are sometimes large enough to be observed with the unaided naked eye. These aggregates are also typically more dense than the surrounding oil mixture from which they precipitated, so they tend to slowly sediment. If the blending of such oils and/or process streams causes the aggregation or precipitation of asphaltenes, then the oils are said to be incompatible as opposed to compatible oils that do not precipitate asphaltenes on blending. Precipitated asphaltenes are not desirable as they are known to foul process equipment when rapidly heated to high temperatures.

SUMMARY OF THE INVENTION

The present invention is a method to disaggregate asphaltenes in petroleum oil mixtures by mild heating. A preferred embodiment of the invention determines the presence of aggregated and unaggregated asphaltenes by irradiating the mixture with neutrons and determining the extent of small angle neutron scattering as a function of wavenumber.

DESCRIPTION OF PREFERRED EMBODIMENT

The present invention includes mild heating to disaggregate asphaltenes in blended petroleum oil mixtures. In a preferred embodiment, the presence of asphaltenes is determined by irradiating the mixture with neutrons and measuring small angle neutron scattering.

The preferred embodiment of the present invention includes sensitive neutron scattering for measuring the presence and quantity of asphaltene aggregates in a petroleum oil or in mixtures of two or more petroleum oils, any component of which may be an unprocessed crude oil or a processed oil derived from petroleum. Since the presence of such aggregates has been linked to fouling and coking in refineries (see U.S. Pat. Nos. 5,997,723 and 5,871,634), an objective measure of the presence of aggregates which may have submicron structures that cannot be detected using ordinary optical microscopy is desirable. By contrast, it is shown that small angle neutron scattering (SANS) is sensitive to asphaltene structures in petroleum mixtures ranging from nanometers to microns in size. In distinction to prior neutron scattering studies of asphaltenes, no contrast enhancing deuteration of any of the components in the mixture is required.

Small angle neutron scattering is a well-established technique, and it is described in the US Department of Commerce publication "National Institute of Standards and Technology (NIST) Cold Neutron Research Facility" (January 1996). A collimated beam of cold neutrons having wavelength λ=5 Å is directed at a test material. A two dimensional array detector placed behind the sample measures the intensity, I, of neutrons scattered by the crude oil mixture as a function of the wavenumber, q, which is related to the angle of scattering away from the transmitted neutron beam, θ, by the equation q=(4π sin (θ/2))/λ. The scattering results from inhomogeneities in the neutron scattering length density, which is related to the scattering cross sections and proximity of the various nuclei, in the test material. Performing SANS on petroleum mixtures held within a quartz cell with a thickness of 2 mm, optimally, has shown that the presence of asphaltene aggregates can be linked to a strong low-q rise in I(q) due to scattering from the surfaces of the aggregates.

Figure 1:
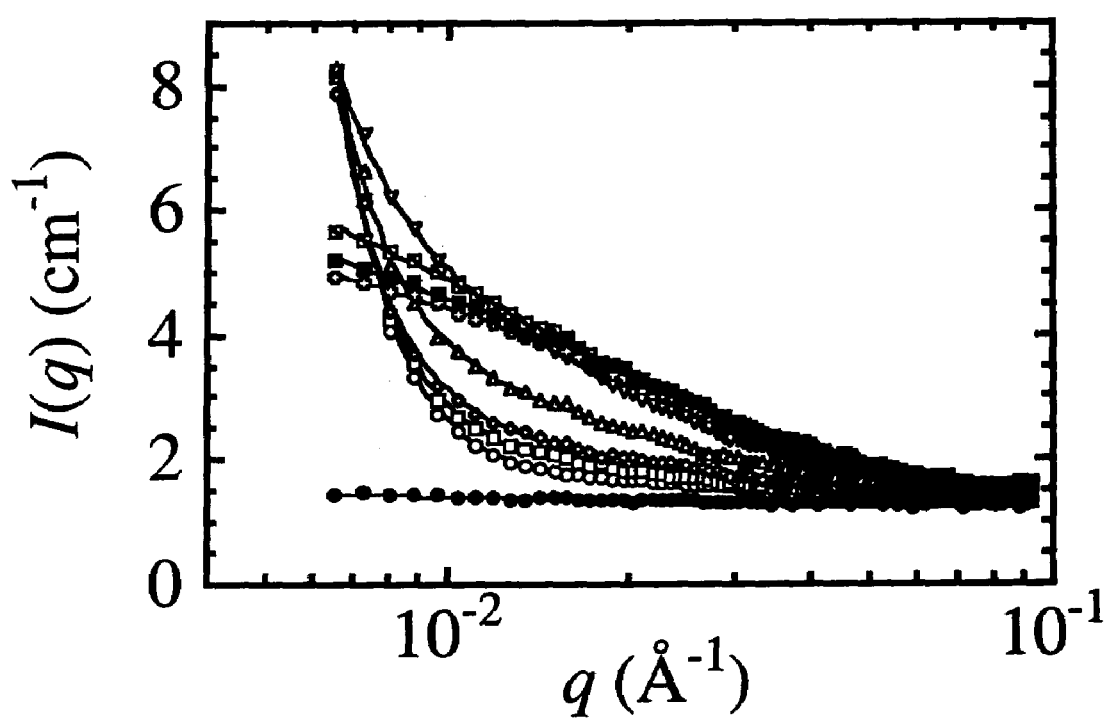
FIG. 1 shows the measured neutron intensity, I, as a function of wavenumber, q, for mixtures of heavy Souedie and light Forties crude oils for several mixing volume fractions, $\phi_m$, of the heavy crude oil in the light crude oil: $\phi_m=0$ or pure Forties oil (solid circles), 0.1 (open circles), 0.2 (open squares), 0.3 (open diamonds), 0.4 (open triangles), 0.5 (open inverted triangles), 0.7 (hatched squares), 0.9 (open crosses), 1.0 or pure Souedie oil (solid squares). The solid lines are fits to Equation (1) to be described later in the specification.
Figure 2:
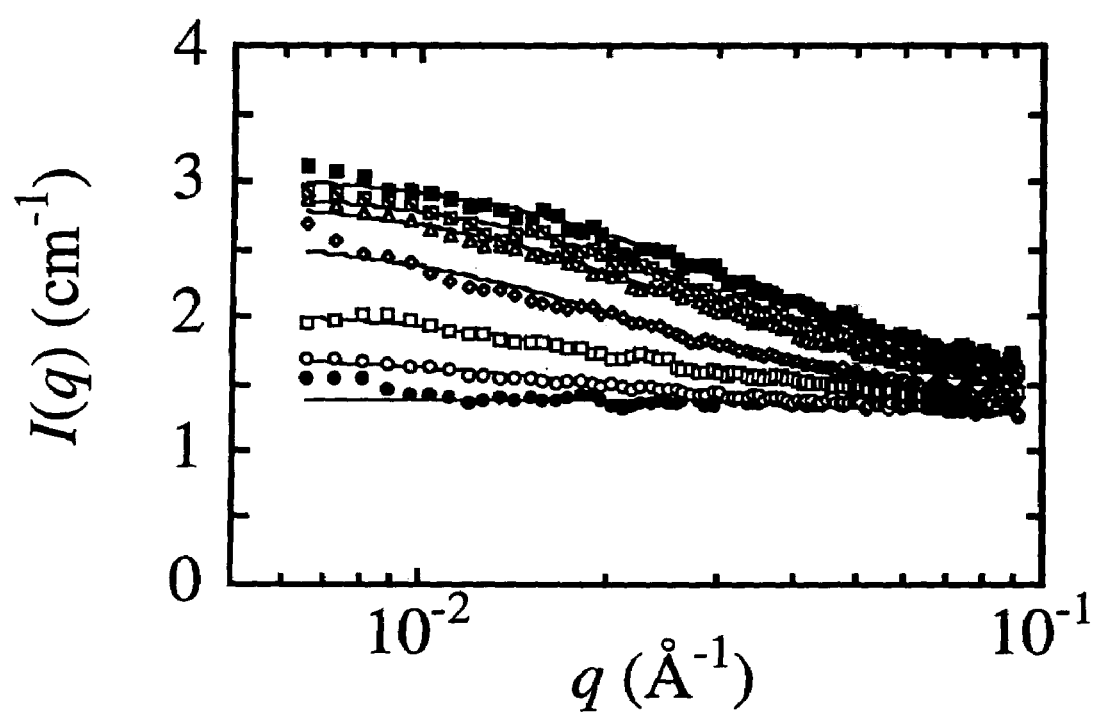
FIG. 2 shows the measured scattered neutron intensity, I, as a function of wavenumber, q, for mixtures of heavy BCF-22 and Marib Light crude oils for several mixing volume fractions, $\phi_m$, of the heavy crude oil in the light crude oil: $\phi_m=0$ or pure Marib Light oil (solid circles), 0.1 (open circles), 0.2 (open squares), 0.4 (open diamonds), 0.6 (open triangles), 0.8 (hatched squares), 1.0 or pure BCF-22 oil (solid squares) in order from bottom to top. The solid lines are fits to Equation (1).

The measured I(q) for a mixture of Souedie (an asphaltene-containing heavy crude oil) and Forties (a lighter paraffinic crude oil) is shown for a series of mixing volume fractions, $\phi_m$, of the heavier Souedie oil in FIG. 1. For compatible $\phi_m$, the shape of I(q) is nearly Lorentzian and the logarithmic slope of I(q), defined as d l n I(q)/d l n q, approaches zero as q approaches zero, indicating that the asphaltenes are in the form of nanometer-sized particles. However, for $\phi_m$ at which the mixture is incompatible, a strong rise is observed toward low q, such that the absolute value of the logarithmic slope of I(q) exceeds three (corresponding to aggregates having surfaces that are fractal or more dense than fractal) as q approaches zero. Based on this logarithmic slope criterion, the range of incompatibility of these crude oils is measured to be $0 < \phi_m \leq 0.52$. This is a larger measured range of incompatibility than has been reported by Wiehe: "Prevention of Fouling by Incompatible Crudes with the Oil Compatibility Model."Proc. AIChE Internat. Conf. Petrol. Phase Behavior and Fouling 1999, 1:354–358 (the range of incompatible mixing volume fractions was reported as $0 < \phi_m \leq 0.33$) and also in U.S. Pat. No. 5,997,723 and potentially quantifies what has been termed "near-incompatible". This reveals the greater sensitivity of the SANS measurement procedure we have employed and, according to drawing 1 in U.S. Pat. No. 5,997,723, mixing at $\phi_m \approx 0.52$ would lead to greatly reduced fouling, whereas mixing at $\phi_m \sim 0.33$ measured by Wiehe and Kennedy using an optical microscopic method would lead to fouling. By contrast, the measured I(q) for two crude oils that are compatible at any mixing volume fraction, BCF-22 and Marib Light, is shown for the same set of $\phi_m$ in FIG. 2. No strong low-q rise in I(q) is observed, consistent with the absence of asphaltene aggregates in the mixtures. This difference in the behavior of the logarithmic slope at low q characterizes the essential difference between compatible and incompatible mixtures. This allows using SANS as a tool for more accurately testing petroleum mixtures. Finally, since Souedie and Forties crude oils contain solid wax particulates, we have shown that SANS can be used to detect asphaltene aggregation despite the presence of solid wax particulates in the oils.

It has also been found that the following equation can be used to fit the measured I(q):

$$I(q)=I_{incoh}+I_L/(1+q^2\xi^2)+I_{surf}(q/q_1)^{-\alpha}, \qquad (1)$$

Here, $I_{incoh}$ is the constant high-q incoherent scattered neutron intensity, $I_L$ is the low-q plateau intensity of the Lorentzian, ξ is the correlation length (proportional to the radius of gyration of an asphaltene particle), $I_{surf}$ is the low-q value of the intensity due to surface scattering from asphaltene aggregates, α is the absolute value of the logarithmic slope of I(q) at low q, and $q_1$ is fixed by the lowest q probed in the experiment. Each of the terms in this equation has a justification in terms of a simple physical model. The constant incoherent scattering term is correlated to the atomic hydrogen to carbon ratio of all the free molecules in the oil. The second Lorentzian term is related to the scattering from unaggregated nanometer-sized asphaltene particles. Finally, the third power law term is due to surface scattering from much larger asphaltene aggregates that have been formed at an earlier time due to the aggregation of a subset of asphaltene particles after the petroleum oils have been mixed together. The fits to the measured I(q) using Equation (1) are shown by the solid lines in FIGS. 1 and 2. The quality of the fits is excellent.

Figure 3:
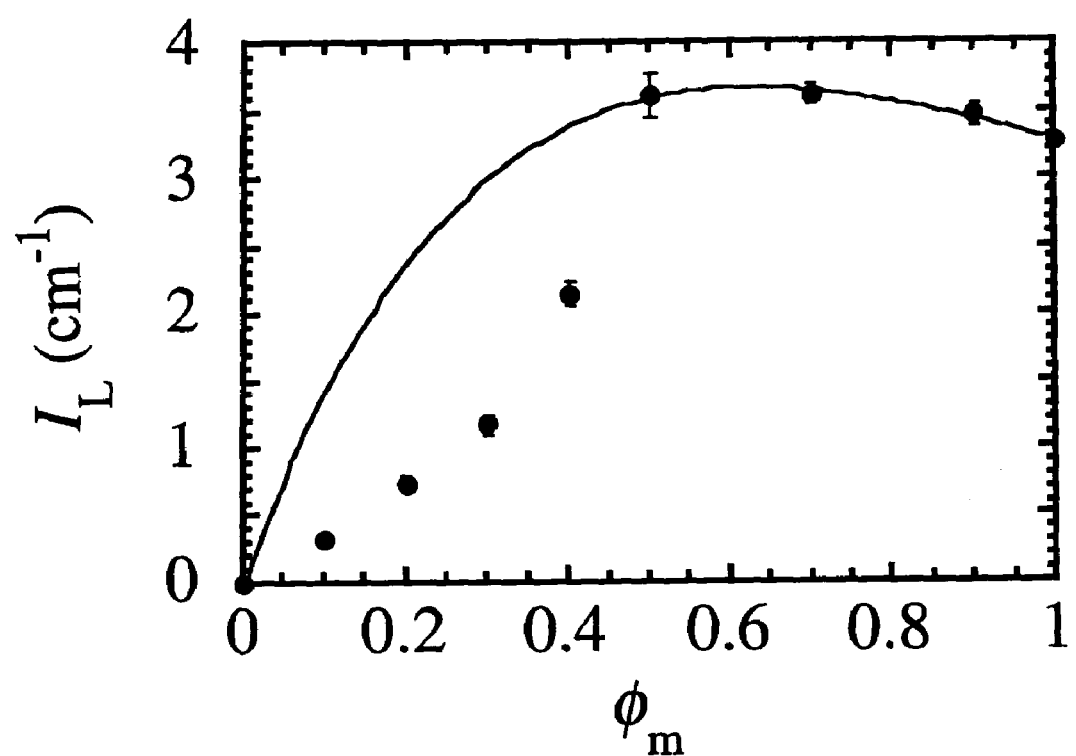
FIG. 3 shows the low-q scattering intensity associated with the Lorentzian term, $I_L$, of Eq. (1) as a function of mixing volume fraction, $\phi_m$, for Souedie/Forties crude oil mixtures, as obtained from fitting the data in FIG. 1. The solid line represents a fit to data for $\phi_m \geq 0.7$ using the hard sphere model of Equation (2), yielding $\phi_u=0.12$.
Figure 4:
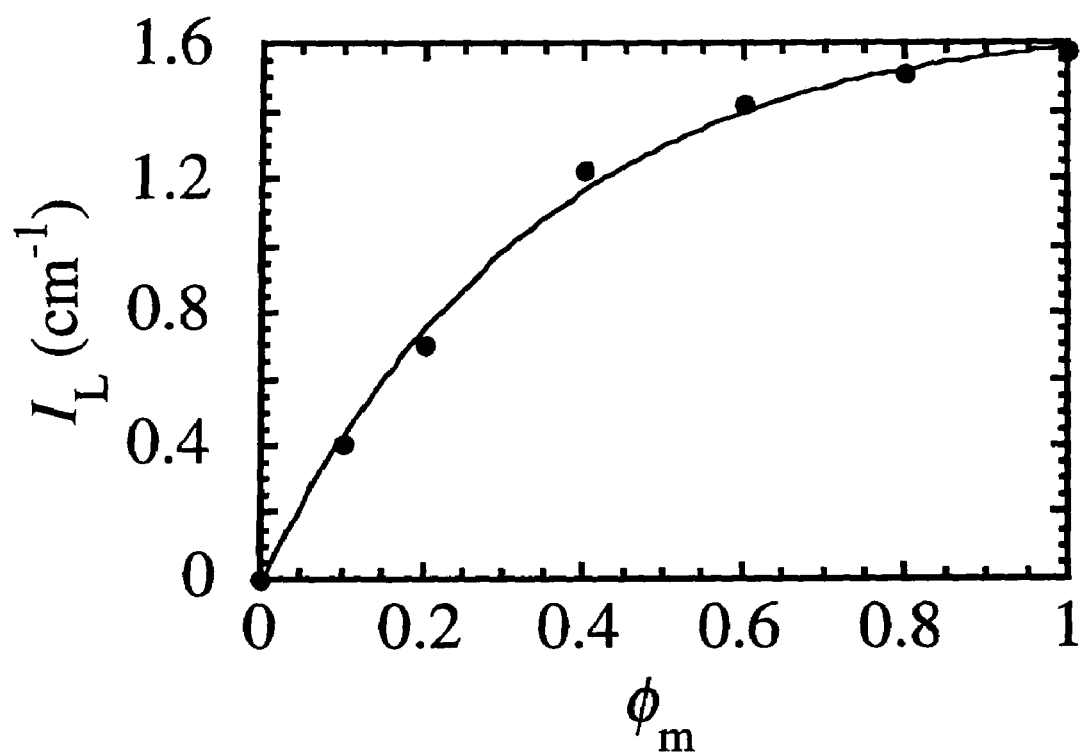
FIG. 4 shows the low-q scattering intensity associated with the Lorentzian term, $I_L$, of Equation (1) as a function of mixing volume fraction, $\phi_m$, for BCF-22/Marib Light crude oil mixtures, as obtained by fitting the data in FIG. 2. The solid line represents a fit of all data using the hard sphere model of Equation (2), yielding an asphaltene particle volume fraction of $\phi_u=0.077$ in the pure BCF-22 oil.

One simple way that neutron scattering can show the incompatibility of a mixture of oils is through the behavior of $I_L(\phi_m)$ for the asphaltene particles obtained by fitting SANS I(q) data using Equation (1), as shown for the Souedie/Forties crude oil mixture by the solid circles in FIG. 3. For low $\phi_m$ where the asphaltenes are effectively in a non-polar solvent (i.e. mostly Forties crude oil), there is a clear upward or positive concavity in $I_L(\phi_m)$ than ends around $\phi_m \approx 0.5$. If one treats the asphaltene particles as spherical particles that interact only through a contact repulsion and considers their structure factor in the low-q dilute limit, then it is possible to calculate an approximate theoretical prediction for the expected behavior of the intensity as a function of $\phi_m$ in the absence of aggregation. The prediction for the behavior of $I_L(\phi_m)$ for perfect hard spheres in the absence of aggregation is given by $I_{HS}(\phi_m)$:

$$I_{HS}(\phi_m) = \frac{I_u \phi_m \phi_u}{[1 + 8a\phi_m \phi_u + 2a(\phi_m \phi_u)^2 + 6b\phi_m \phi_u]}, \quad (2)$$

where the denominator represents the hard sphere structure factor $S(q,\phi_m)$ in the limit as $q \to 0$, $a=(1+2\phi_m\phi_u)^2/(1-\phi_m\phi_u)^4$, $b=(1+\phi_m\phi_u/2)^2/(1-\phi_m\phi_u)^4$, $\phi_u$ represents the effective hard sphere volume fraction of asphaltenes in the undiluted oil at $\phi_m=1$, and $I_u$ represents the scattering intensity from the unaggregated "hard sphere" asphaltenes. As shown in FIG. 3 by the solid line, this theoretical prediction of Equation (2) only fits the data for $\phi_m > 0.5$. The lack of agreement at low $\phi_m$ is a clear indicator that the population of suspended asphaltene particles has become depleted due to aggregation. By contrast, for a compatible crude oil mixture, BCF-22 and Marib Light, Equation (2) provides a good fit to $I_L(\phi_m)$ over the entire range $0 \leq \phi_m \leq 1$, and the concavity is clearly a downward or negative concavity, as shown in FIG. 4. Different systematic trends in the behavior of the correlation length associated with the particles as a function of $\phi_m$ can also be used to distinguish between compatible and incompatible mixtures and determine the range of incompatibility.

Figure 5:
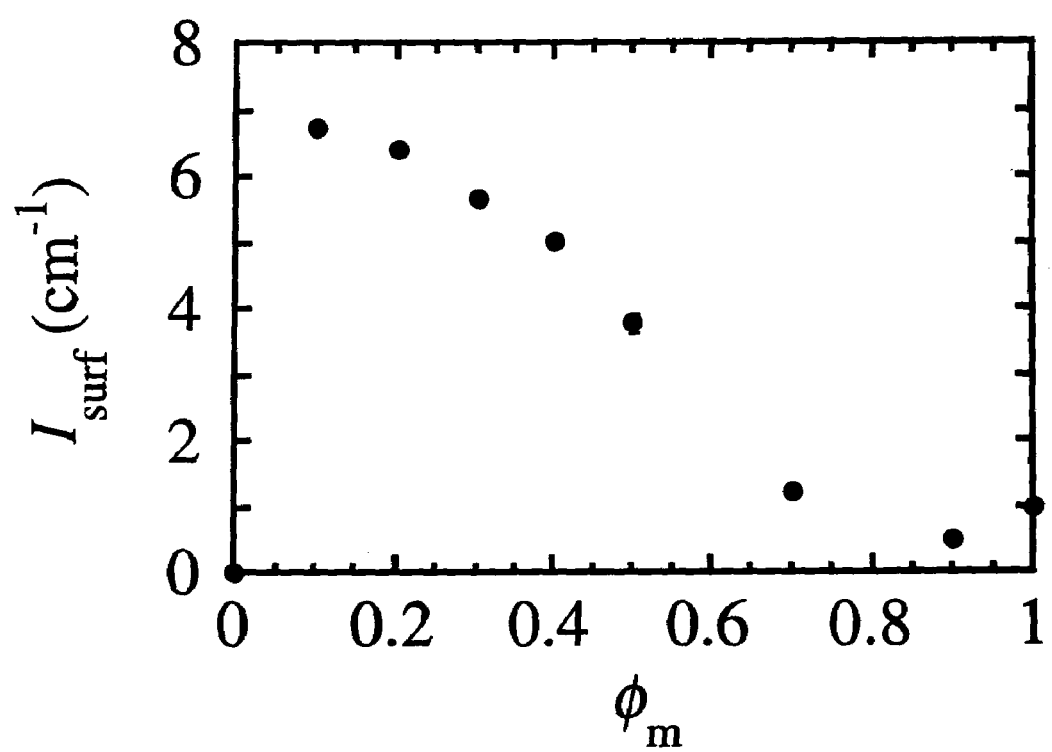
FIG. 5 shows the low-q scattering intensity, $I_{surf}$, associated with surface scattering from asphaltene aggregates of Equation (1) as a function of mixing volume fraction, $\phi_m$, for Souedie/Forties crude oil mixtures, as obtained by fitting the data in FIG. 1.
Figure 6:
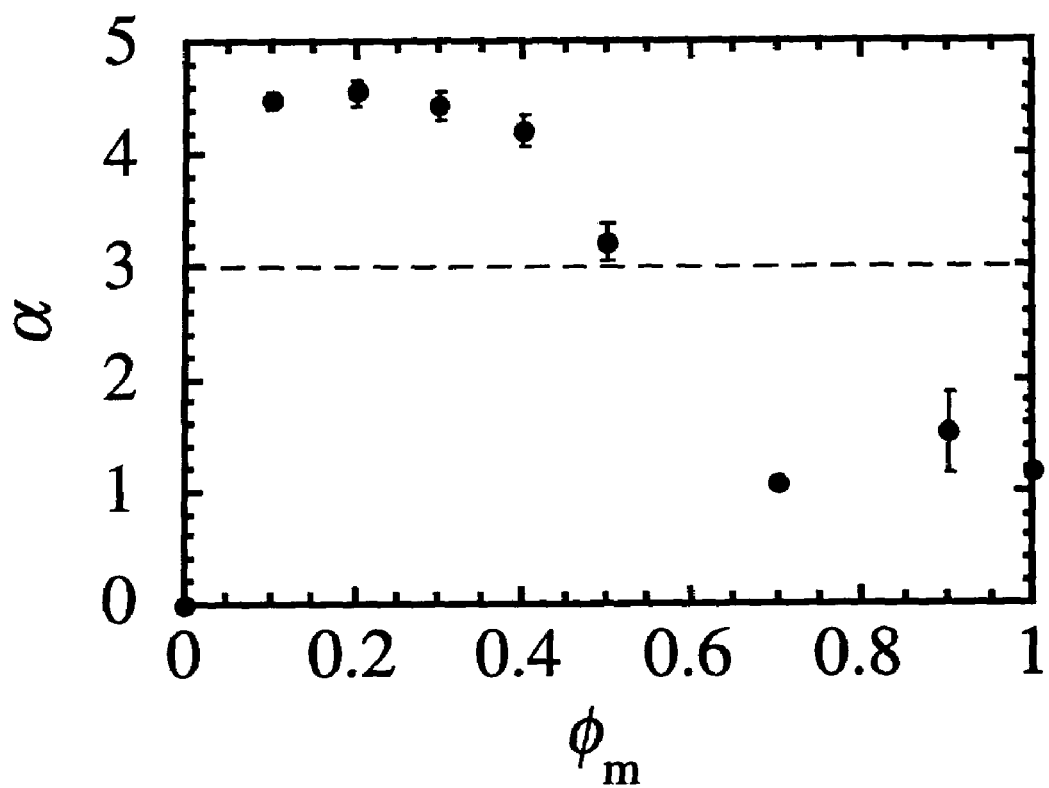
FIG. 6 shows the power law exponent associated with surface scattering from asphaltene aggregates, $\alpha$, of Equation (1) as a function of mixing volume fraction, $\phi_m$, for Souedie/Forties crude oil mixtures, as obtained by fitting the data in FIG. 1. The value of a is essentially the absolute value of the slope of I(q) on a log-log plot in the low q limit. The dashed line represents $\alpha=3$, a criterion for determining if asphaltene aggregates are present, as described later in the specification.

The incompatibility of the mixtures can also be detected more directly through the surface scattering intensity, $I_{surf}$, and the power law exponent, $\alpha$, that arise from the change in the neutron scattering length density at the asphaltene aggregates' surfaces. As an example, for incompatible mixtures such as Souedie/Forties, the surface scattering intensity, shown in FIG. 5, rises rapidly from zero at $\phi_m=0$ to a large finite value that is significantly greater than $I_L$ for the pure heavy crude oil for $\phi_m > 0$. It then decreases thereafter for larger $\phi_m$, and when $I_{surf}(\phi_m)$ becomes less than $I_L(\phi_m)+I_{incoh}(\phi_m)$, one has reached the limit of incompatibility. For this mixture, this boundary occurs a little above $\phi_m=0.5$. This criterion for determining aggregation from $I_{surf}$ compared to $I_L+I_{incoh}$ can be applied to a single SANS I(q) measurement at a particular $\phi_m$ without the need for an entire set of measurements as a function of $\phi_m$. Likewise, the value of the power law exponent, $\alpha$, can be used to determine the boundary of incompatibility; $\alpha > 3$ defines the existence of aggregates with surface structures that are at least fractal in nature, as shown in FIG. 6 for the Souedie/Forties crude oil mixture. The boundary for incompatibility using this criterion for $\alpha$ yields a value for the limit of incompatibility of $\phi_m \approx 0.52$ that is in agreement with the other criteria.

In addition to assessing incompatibility of petroleum oils, it is possible to estimate the volume fraction of the asphaltene aggregates, $\phi_{agg}$, and the average length scale, R, associated with the internal structures of the aggregates from the fits to $I(q,\phi_m)$ using Equation (1). The difference between the values for the fitting parameter $I_L$ and the hard sphere prediction $I_{HS}$ given by the solid line in FIG. 3 in the incompatible region can be used to estimate $\phi_{agg}$ in a crude oil mixture:

$$\phi_{agg}(\phi_m) = \phi_u \phi_m [I_{HS}(\phi_m) - I_L(\phi_m)]/I_{HS}(\phi_m). \quad (3)$$

Figure 7:
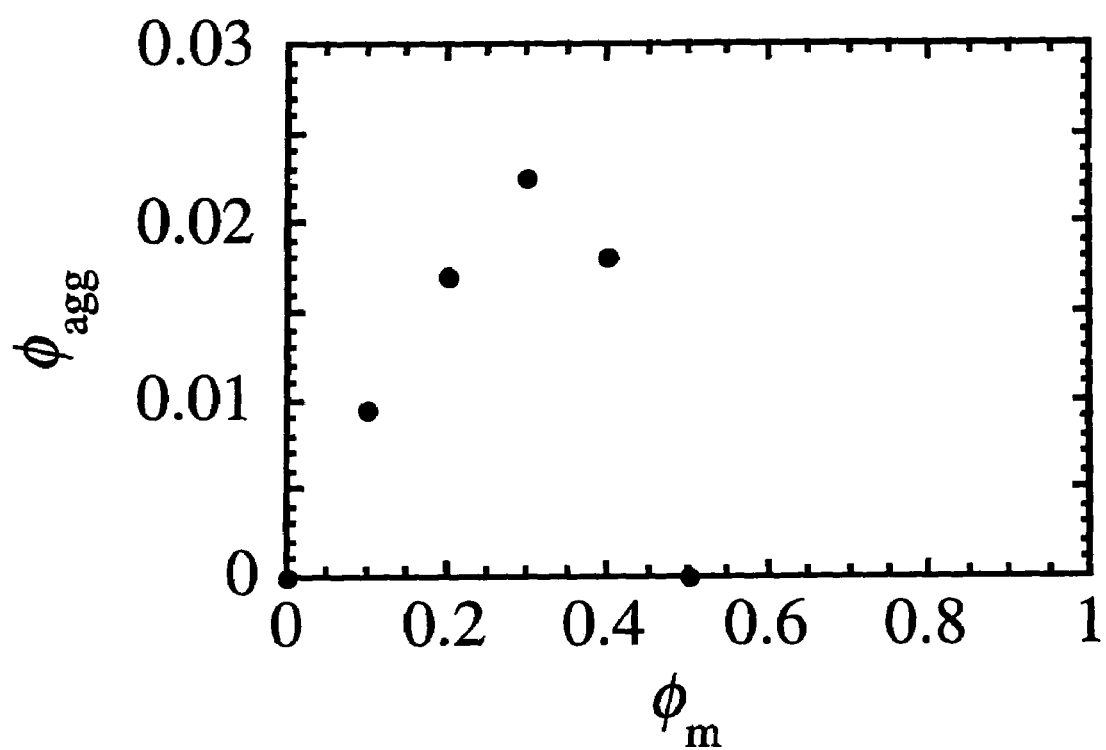
FIG. 7 shows the volume fraction of aggregated asphaltenes, $\phi_{agg}$, as a function of the volume fraction of mixing, $\phi_m$, for Souedie/Forties crude oil mixtures, as obtained from the difference between the measured $I_L$ and the hard sphere prediction for $I_L$ in FIG. 3, as described by Equation (3) later in the specification.

The results of this calculation for the Souedie/Forties are shown in FIG. 7 and indicate that the maximum volume fraction of aggregates occurs near the center of the incompatible region around $\phi_m \approx 0.3$. Once the aggregate volume fraction is known, the average length scale, R, of the internal structures of the aggregates can be estimated using the total surface area of the aggregates per unit volume of the oil, $S_V$, that can be obtained from $I_{surf}$: $R \approx 3\phi_{agg}/S_V$, using the approximation that the internal structures are interconnected spheres of radius R. The well-known Porod scattering law from a step change in the neutron scattering length density of $\Delta\rho$ at the boundary between an asphaltene aggregate and the surrounding liquid oil mixture gives an expression for $S_V$: $S_V = I_{surf}/(2\pi\Delta\rho^2 q_1^{-4})$, so R is:

$$R \approx 6\pi\phi_{agg}\Delta\rho^2 q_1^{-4}/I_{surf}. \quad (4)$$

Figure 8:
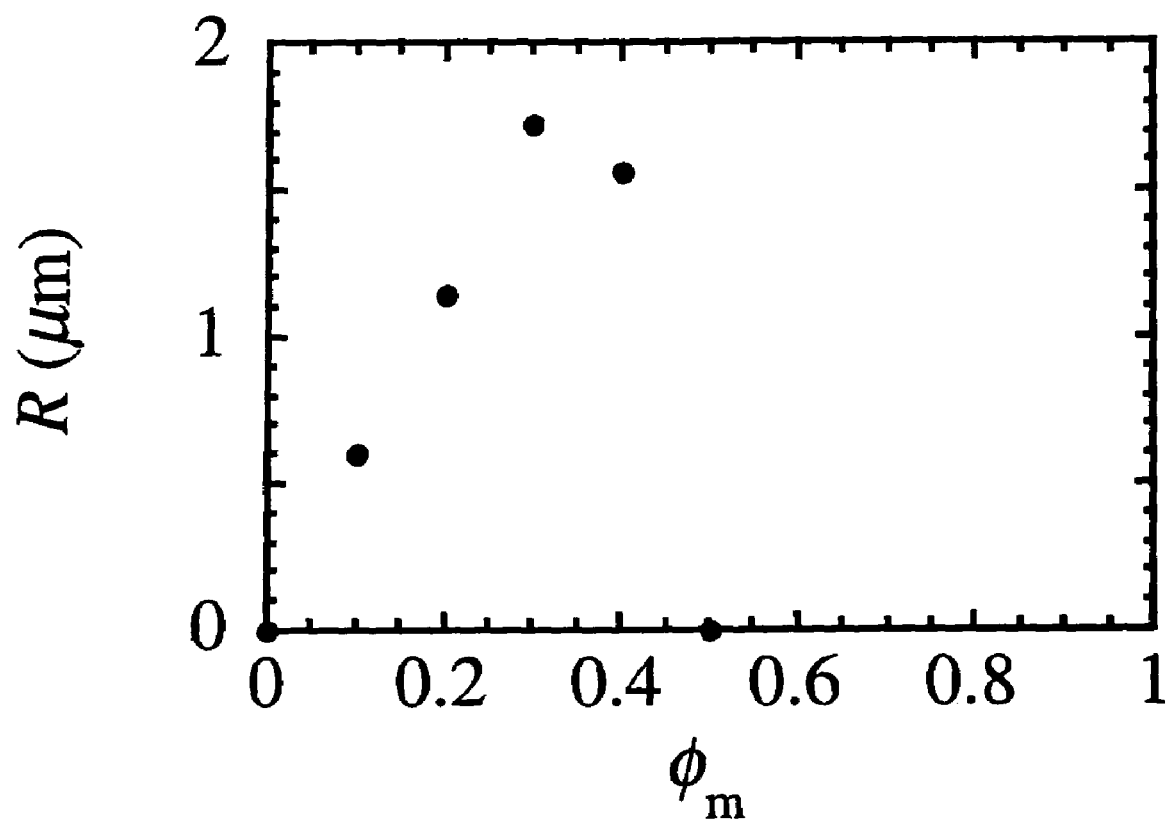
FIG. 8 shows the characteristic length scale of compact structures within asphaltene aggregates, R, as a function of the volume fraction of mixing, $\phi_m$, for Souedie/Forties crude oil mixtures, as calculated using Equation (4) from $I_{surf}$ and $\phi_{agg}$ shown in FIGS. 5 and 7, respectively.

For example, for the Souedie/Forties crude oil mixture at $\phi_m=0.4$, where $\alpha \approx 4$, $I_{surf}=5$ cm$^{-1}$, and $\phi_{agg}=0.018$, we estimate $S_V=355$ cm$^{-1}$ and $R \approx 1.5$ μm for typical values of $\Delta\rho=2\times10^{10}$ cm$^{-2}$ and $q_1=6.5\times10^{-3}$ Å$^{-1}$. Using a more general approach that resembles this in form but accounts for a more gradual non-step change in the neutron scattering length density, we can account for non-Porod values of $\alpha$, and the values of R determined for the Souedie/Forties crude oil mixture are shown in FIG. 8. The actual spatial extent of the aggregates can be much larger than the average internal structure length R.

The aggregated asphaltenes found in incompatible petroleum oil mixtures may be disaggregated through mild heating before introducing such mixtures into the extremely hot environment of refinery furnaces in order to inhibit the deposition and coking of carbonaceous material on the walls of the furnaces. The mild preheating may be accomplished in several ways: blending the crude oils together in-line at an elevated temperature or taking a petroleum oil or petroleum oil mixture that contains asphaltene aggregates and mildly heating it in a tank for up to several hours before introducing the petroleum oil into the very hot refinery furnace. Since asphaltenes comprise a set of molecules having highly varied atomic contents, structures, and molecular weights, the mild preheating may be effective enough to cause substantial, if not total, disaggregation of the asphaltene aggregates, depending upon the temperature and the time that the petroleum oil or oil mixture has been held at that temperature. Even a partial disaggregation of the asphaltenes by mild heating could be useful since the rate of fouling of process equipment linked to the quantity of aggregated (i.e. unsuspended) asphaltenes in the stream.

Figure 9:
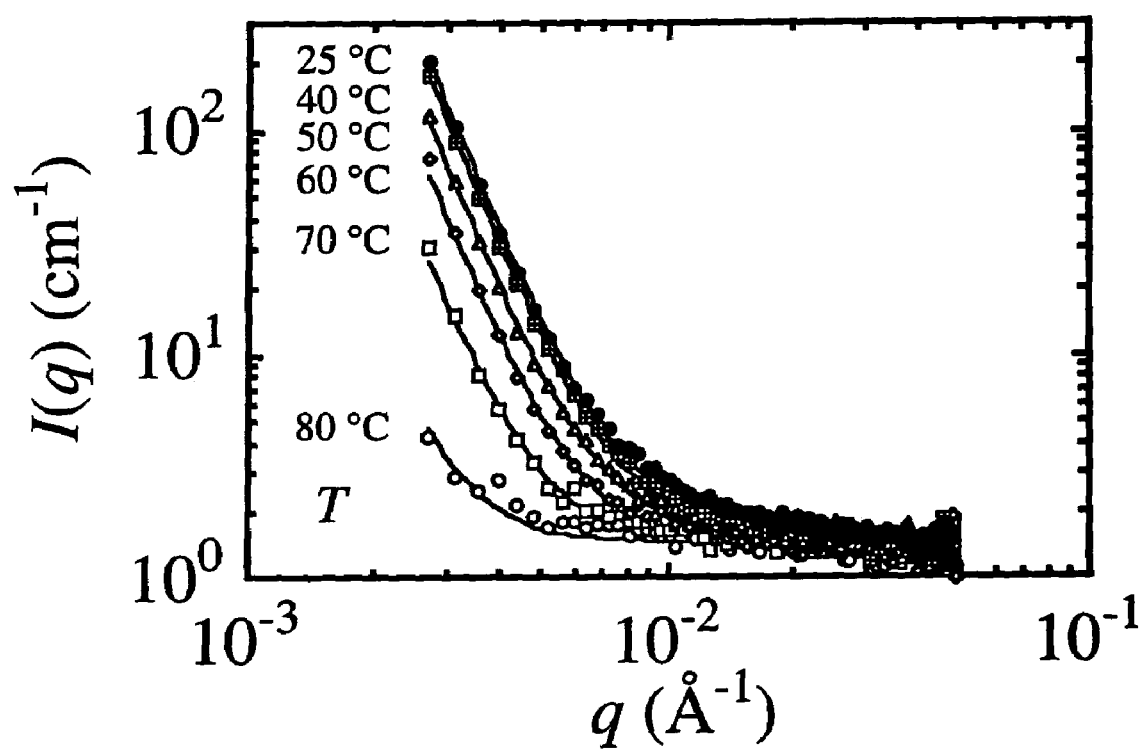
FIG. 9 shows the measured scattered neutron intensity, I, as a function of wavenumber, q, for a Souedie/Forties crude oil mixture at a Souedie volume fraction of $\phi_m=0.2$ at the following temperatures: T=25° C. (solid circles), 40° C. (crossed open squares), 50° C. (open triangles), 60° C. (open diamonds), 70° C. (open squares), 80° C. (open circles). The solid lines are fits using Equation (1), as described later in the specification.
Figure 10:
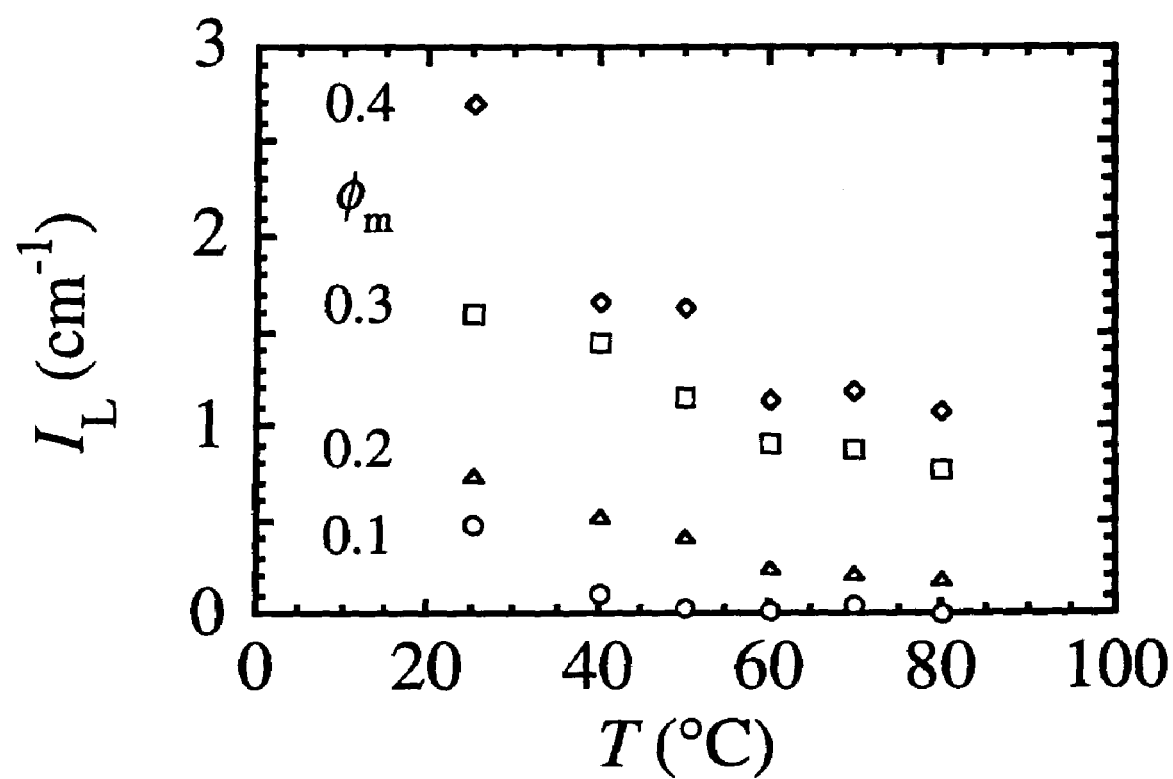
FIG. 10 shows the temperature dependence of the plateau intensity associated with the Lorentzian feature, $I_L$, of asphaltene particles for $\phi_m$=0.1 (open circles), 0.2 (open triangles), 0.3 (open squares), and 0.4 (open diamonds). The values have been determined using Equation (1) to fit the temperature-dependent I(q) for the different mixing volume fractions.
Figure 11:
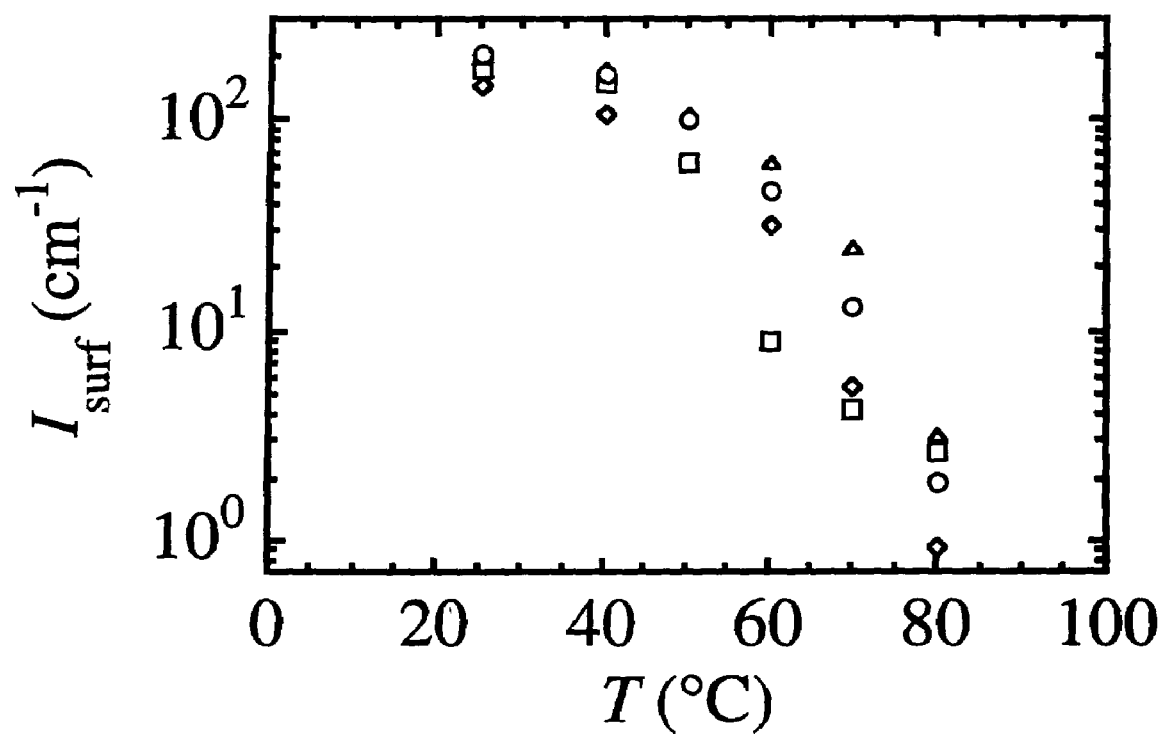
FIG. 11 shows the temperature dependence of the low-q value of the surface scattering intensity from the asphaltene aggregates, $I_{surf}$, for $\phi_m$=0.1 (open circles), 0.2 (open triangles), 0.3 open squares), and 0.4 (open diamonds). The values have been determined using Equation (1) to fit the temperature-dependent I(q) for the different mixing volume fractions, and these values are nearly identical to the measured $I(q_1)$ at each $\phi_m$ and T.
Figure 12:
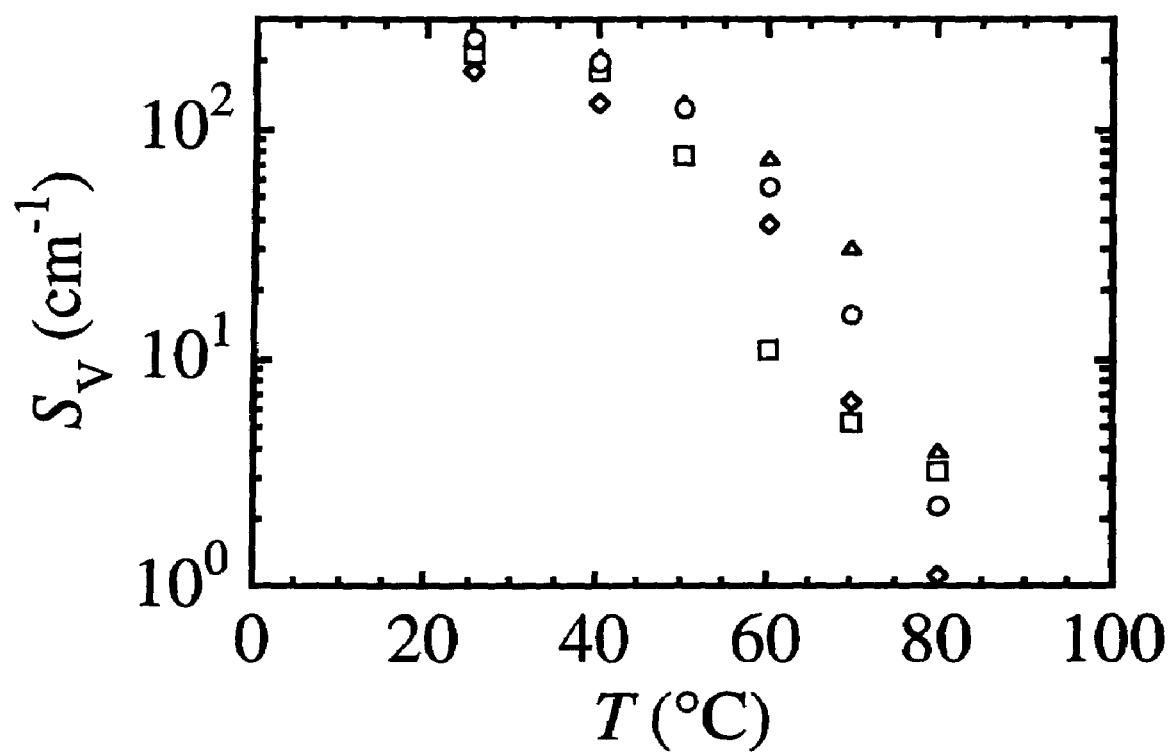
FIG. 12 shows the temperature dependence of the surface-to-volume ratio of asphaltene aggregates, $S_V$, for $\phi_m$=0.1 (open circles), 0.2 (open triangles), 0.3 (open squares), and 0.4 (open diamonds), determined using the values for $I_{surf}$ shown in FIG. 11, and using an equation described later in the specification.

Using small angle neutron scattering as described above, the disaggregation of the asphaltenes in a Souedie and Forties crude oil mixture has been observed as the temperature is raised from room temperature to T=80° C. In this measurement, the lowest q set by the detector distance from the sample cell was $q_1=2.7\times10^{-3}$ Å$^{-1}$. By increasing the temperature in a stepwise fashion, and then measuring the scattered neutron intensity, I, as a function of wavenumber, q, after about 50 minutes at a given temperature, T, a dramatic reduction in the low-q scattered intensity has been shown when the temperature exceeds roughly T>70° C. An example of the reduction in surface scattering from asphaltene aggregates due to mild heating for a mixing volume fraction of twenty percent Souedie crude oil in Forties crude oil ($\phi_m=0.2$) is shown in FIG. 9. The solid lines in FIG. 9 are fits to the data using Equation (1). The heating causes a systematic reduction in the Lorentzian plateau value, $I_L$, for a set of Souedie/Forties crude oil mixtures having different $\phi_m$ in the incompatible region, as shown in FIG. 10, and it also causes a more dramatic reduction in $I_{surf}$ and $S_V$ as shown in FIGS. 11 and 12, respectively. Since $\phi_{agg}$ is proportional to $I_{surf}$ as indicated in Equation (4), this reduction in the low-q scattering clearly indicates that the asphaltene aggregates have mostly disaggregated and that the asphaltenes have been thermally resuspended in the mixture. More fundamentally, this indicates that, by raising the temperature, the depth of the attractive well in the average interaction potential between the asphaltenes has been reduced so as to be comparable to or less than thermal energy, thereby causing most of the asphaltenes to redisperse. Although we have demonstrated the disaggregation of asphaltene aggregates after mild heating using the technique of SANS, other techniques, including some optical techniques, can also be used to show this effect. Similarly, other beamline techniques, such as ultra small angle neutron scattering (USANS) an extension of SANS to lower q than those in the examples we show, could be employed to detect disaggregation after heating.

The advantage of the mild pre-heating method over the other methods is that it does not require the addition of a potentially costly dispersant and that the temperature should be easily accessible in a refinery environment. The kinetics of the disaggregation is fast enough that a simple warm holding tank approach for previously mixed oils or even in-line mixing of pre-warmed oils are feasible approaches. Finally, this approach may potentially be used with so-called self-incompatible crude oils, namely, those crude oils that inherently contain asphaltene aggregates as a result of their production and not due to mixing with other petroleum oils. Thus, it may be possible to use self-incompatible crude oils or petroleum oil mixtures in which asphaltene aggregates are known to exist in a refinery equipped with the pre-heating disaggregation process step.

Suitable time/temperature ranges for the heating step include 1 minute to four weeks at a temperature between 40 and 150° C., or a preferred range of 2 minutes to 24 hours at a temperature between 40 and 100° C., a more preferred range of 3 minutes to 3 hours at a temperature between 40 and 80° C., a most preferred range of 4 minutes to 1 hour at a temperature between 40 and 60° C.

What is claimed is:

1. A method comprising determining the presence of asphaltene aggregates by irradiating said petroleum oils and oil mixtures of petroleum oils, feedstream and/or refinery process streams with neutrons and determining small angle neutron scattering (SANS) intensity, I, as a function of wavenumber, q, wherein said scattering intensity includes a coherent component and an incoherent component.

2. The method of claim 1 wherein said neutron scattering wavenumber, q, is in the range $10^{-4}$ Å$^{-1}$ $\leq q \leq 1$ Å$^{-1}$.

3. The method of claim 2 wherein compatibility and incompatibility of petroleum oils and mixtures of petroleum oils and/or refinery process streams are determined fitting I(q) to an equation based on a physical model that contains coherent components, a strongly decaying component to describe the surface scattering of asphaltene aggregates at the q near its lower range (low-q), a plateau component with a falloff for q near its upper range (high-q) to describe the asphaltene particles, and a constant to describe the q incoherent component.

4. The method of claim 3 wherein the equation is given by $$I(q)=I_{incoh}+I_L/(1+q^2\xi^2)+I_{surf}(q/q_1)^{-\alpha}$$

Wherein, $I_{incoh}$ is the constant high-q incoherent scattered neutron intensity, $I_L$ is the low-q plateau intensity of the Lorentzian (second term), $\xi$ is the correlation length (proportional to the radius of gyration of an asphaltene particle), $I_{surf}$ is the low-q value of the intensity due to surface scattering from asphaltene aggregates, $\alpha$ is the absolute value of the logarithmic slope of I(q) at low q, and $q_1$ is fixed by the lowest q in the range.

5. The method of claim 4 wherein incompatibility is determined by the concavity of the low-q plateau intensity of the asphaltene particles, $I_L$, as a function of the volume fraction of mixing, $\phi_m$.

6. The method of claim 4 wherein incompatibility is determined by the systematic deviation of $I_L$, as a function of mixing volume fraction from a hard sphere prediction.

7. The method of claim 4 wherein incompatibility is determined by a maximum in the correlation length, $\xi$.

8. The method of claim 4 wherein incompatibility is determined by the dominance of the low-q value of the surface scattering intensity, $I_{surf}$ over the sum of the low-q plateau intensity of the asphaltene particles, $I_L$, and the incoherent scattering intensity, $I_{incoh}$.

9. The method of claim 4 wherein incompatibility is determined by the power law exponent, $\alpha$, exceeding a value of three.

10. A method to estimate the volume fraction of asphaltene aggregates, $\phi_{agg}$, in incompatible petroleum oil and/or refinery process stream mixtures comprising determining the difference between $I_L$, the low-q plateau intensity corresponding to the asphaltene particles and $I_{HS}$, the intensity perfect hard spheres in the absence of aggregation, wherein $I_L$, and $I_{HS}$ are determined at different volume fractions of mixing $\phi_m$.

11. The method of claim 10 wherein the equation to estimate the volume fraction of asphaltene aggregates, $\phi_{agg}$, is given by the difference between the measured valve of $IL(\phi_m)$ and the $I_L(\phi_m)$ for perfect hard spheres in the absence of aggregation.

12. The method of claim 4 wherein the total surface area of asphaltene aggregates per unit volume of the petroleum oil, $S_V$, is determined from the surface scattering intensity, $I_{surf}$ at low wavenumbers, q.

13. The method of claim 11 wherein the average length scale, R, associated with the internal structures of the asphaltene aggregates is determined from the ratio of the volume fraction of asphaltene aggregates and the total surface area of asphaltene aggregates, wherein the total surface of asphaltene aggregates per unit volume of the petroleum oil, $S_V$, is determined from the surface scattering intensity, $I_{surf}$ at low wavenumbers, q.

14. The method of claim 1 wherein said neutron scattering wavenumber, q, is in the range $10^{-3}$ Å$^{-1}$ $\leq q \leq 10^{-1}$ Å$^{-1}$.

* * * * *